(12) United States Patent
Duggirala et al.

(10) Patent No.: US 9,063,080 B2
(45) Date of Patent: Jun. 23, 2015

(54) METHOD OF DEPOSITION MONITORING

(71) Applicant: Ecolab USA Inc., Naperville, IL (US)

(72) Inventors: Prasad Y. Duggirala, Naperville, IL (US); Sergey M. Shevchenko, Aurora, IL (US); Michael J. Murcia, DeKalb, IL (US)

(73) Assignee: ECOLAB USA INC., Naperville, IL (US)

( * ) Notice: Subject to any disclaimer, the term of this patent is extended or adjusted under 35 U.S.C. 154(b) by 144 days.

(21) Appl. No.: 13/952,395

(22) Filed: Jul. 26, 2013

(65) Prior Publication Data
US 2015/0029496 A1    Jan. 29, 2015

(51) Int. Cl.
*G01N 21/41* (2006.01)
*G01N 21/43* (2006.01)
*G01N 17/00* (2006.01)
*G01N 21/94* (2006.01)

(52) U.S. Cl.
CPC ............... *G01N 21/43* (2013.01); *G01N 21/41* (2013.01); *G01N 21/4133* (2013.01); *G01N 17/008* (2013.01); *G01N 21/94* (2013.01); *G01N 2021/945* (2013.01)

(58) Field of Classification Search
CPC .... G01N 21/41; G01N 21/4133; G01N 21/43
USPC .................................................. 356/128, 134
See application file for complete search history.

(56) References Cited

U.S. PATENT DOCUMENTS

| | | | |
|---|---|---|---|
| 3,433,603 | A | 3/1969 | Jeffery |
| 4,571,075 | A | 2/1986 | Kamrat |
| 4,776,697 | A | 10/1988 | Kamrat |
| 5,001,938 | A | 3/1991 | Downie |
| 5,254,286 | A | 10/1993 | Gill et al. |
| 5,734,098 | A | 3/1998 | Kraus et al. |
| 5,815,264 | A | 9/1998 | Reed et al. |
| 5,859,705 | A | 1/1999 | Benedetto et al. |
| 6,053,032 | A | 4/2000 | Kraus et al. |
| 6,250,140 | B1 | 6/2001 | Kouznetsov et al. |
| 6,387,705 | B1 | 5/2002 | Claibourn et al. |
| 6,819,419 | B2 | 11/2004 | Jaaskelaimen |
| 6,942,782 | B2 | 9/2005 | Shevchenko et al. |
| 7,094,562 | B2 | 8/2006 | Bittner |
| 7,175,715 | B2 | 2/2007 | Eiermann |
| 7,482,591 | B2 | 1/2009 | Herrington et al. |
| 7,492,447 | B2 * | 2/2009 | Nakajima et al. ............. 356/128 |
| 7,985,318 | B2 | 7/2011 | Shevchenko et al. |

(Continued)

OTHER PUBLICATIONS

Severtson et al., Tappi J., Mechanism and chemical control of CaCO3 scaling in the kraft process, vol. 82 Issue 6, pp. 167-174 (1999).

(Continued)

*Primary Examiner* — Kara E Geisel
*Assistant Examiner* — Hina F Ayub
(74) *Attorney, Agent, or Firm* — Benjamin Carlsen

(57) ABSTRACT

The invention provides methods and compositions for measuring the formation of scale within a process system. The method involves measuring changes in the cell fouling as reflected on the refraction index measurements of a liquid medium with a refractometer and determining the scale formation from changes in the cell fouling factor. This allows for a refractometer to determine the formation of scale in locations that otherwise would not be measurable.

19 Claims, 7 Drawing Sheets

(56) References Cited

U.S. PATENT DOCUMENTS 8,303,768 B2 11/2012 Shevchenko et al.
2002/0070337 A1 6/2002 Fitzgerald

OTHER PUBLICATIONS

Amjad, Mineral scale formation and inhibition. Plenum, N.Y. pp. 32-87 (1995).
Markam et al., Formation of calcium carbonate scale in a Kamyr digester, Proc. TAPPI Pulping Conf., TAPPI Press, 17-21 (1979).
Smith, J. B. et al., Evaluation of sodium salt scaling in a pilot falling film evaporator. TAPPI Pulping/Process, Prod. Qual. Conf., pp. 1013 to 1022, 2001.
Smith, J.B. et al., Quantifying burkeite scaling in a pilot falling film evaporator, TAPPI Pulping Conf., pp. 898 to 916, 2001.
Wallace, Andrew D. et al., Assessment of an Intrinsic Optical Fiber Sensor for in Situ Monitoring of Scale-Forming Salts, Industrial & Engineering Chemistry Research, vol. 47 Issue 4, pp. 1066-1070 (2008).
Adams et al., Low-cost evaporator upgrades boost performance, reduce scaling, R.W., Pulp Paper, vol. 73 Issue 2, pp. 83-89 (1999).
Sithole, Scale deposit problems in pulp and paper mills, African Pulp and Paper Week, Durban, SA (2002).
Sithole, The effects of wood extractives on system closure, TAPPSA Journal, vol. 9, (2002).
Cowan, Water-Formed Scale Deposits, Gulf Publ. Co., Houston, TX (1976) pp. 93-132 (and cover page).
Garver et al., Measuring the response of pitch control strategies, T.M., Yuan, H, Pulp Paper Canada, vol. 103 Issue 9, pp. 24-28 (2002).
Douek et al., The distribution of calcium in kraft mill brownstock systems, by vol. 83 Issue 15, pp. 425-429 (1980).
Smith, J. B. & Hsieh, J. S., Preliminary investigation into factors affecting second critical solids black liquor scaling. TAPPI Pulping/Process, Prod. Qual. Conf., pp. 1 to 9, 2000.

* cited by examiner

METHOD OF DEPOSITION MONITORING

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

The invention relates to methods and apparatuses for the monitoring deposition from an aqueous solution on the surfaces of process equipment. More specifically, the invention relates to a method of monitoring scale deposition from black liquor in pulp mill digesters, evaporators and concentrators. The invention has particular relevance to monitoring and inhibiting scale deposition in pulp mill digesters, evaporators and concentrators to improve process efficiency in pulping operations.

The kraft pulping process is one of the major pulping processes in the pulp and paper industry. Spent liquor resulting from the kraft pulping process (black liquor or "BL") contains various organic materials as well as inorganic salts, the deposition of which detracts from an efficient chemical pulping and recovery cycle due to decreasing thermal conductivity and lengthy boilouts. Other, less common pulping processes such as alkaline or sulfite pulping differ from the kraft process in the chemical composition of the liquor that affect the composition of the deposits.

The most common scale in the pulp and paper industry is calcium carbonate that is also a prevalent scale in many other industries (Amjad, Z. (Ed.) Mineral scale formation and inhibition. Plenum, N.Y. (1995); Cowan, J. C., Weintritt, D. J. Water-Formed Scale Deposits. Gulf Publ. Co., Houston, Tex. (1976)). It is an especially severe problem in kraft digesters (Markham, L. D., Bryce, J. R. G., Formation of calcium carbonate scale in a Kamyr digester, Proc. TAPPI Pulping Conf., TAPPI Press, 17-21 (1979); Severtson, S. J., Duggirala, P. Y., Carter, P. W., Reed, P. E. Mechanism and chemical control of CaCO3 scaling in the kraft process. TAPPI J., 82(6), 167-174 (1999); Sitholé, B. Scale deposit problems in pulp and paper mills. Proc. African Pulp and Paper Week, Durban, S A (2002)). Normally, it is not possible to fully inhibit the precipitation of calcium carbonate due to high driving force. Successful approaches to inhibiting deposition rely on making the deposit non-adherent and dispersed, or sequestration of the calcium ions. Calcium carbonate deposition can be temperature- or pH-induced. While temperature induction is typical of digesters and evaporators, at the bleach plant calcium carbonate scale is more often induced by alkalization. A wide spectrum of calcium carbonate treatment products is available, because their relative performance depends on the conditions, and the applicability depends on the issues of stability and environmental regulations.

Calcium carbonate deposits form extensively at many stages of the papermaking process. As described for example in U.S. Pat. Nos. 7,985,318, 6,053,032, 6,942,782, 6,250,140, and 5,734,098, inorganic salt scaling in spent liquor evaporators and concentrators continues to be one of the most persistent problems encountered in the pulp and paper industry. Concentrated liquor contains calcium, sodium, carbonate, and sulfate ions at levels high enough to form scales that precipitate from solution and deposit on heated surfaces. The most important types of scale in evaporators are hard scale, such as calcium carbonate ($CaCO_3$), and soft scale, such as burkeite ($2(Na_2SO_4):Na_2CO_3$). The solubility of both types of scale decreases as temperature increases, which causes the scales to adhere to heat transfer surfaces thus drastically reducing the overall efficiency of the evaporator (See Smith, J. B. & Hsieh, J. S., Preliminary investigation into factors affecting second critical solids black liquor scaling. TAPPI Pulping/Process, Prod. Qual. Conf., pp. 1 to 9, 2000 and Smith, J. B. & Hsieh, J. S., Evaluation of sodium salt scaling in a pilot falling film evaporator. TAPPI Pulping/Process, Prod. Qual. Conf., pp. 1013 to 1022, 2001; and Smith, J. B. et al., Quantifying burkeite scaling in a pilot falling film evaporator, TAPPI Pulping Conf., pp. 898 to 916, 2001).

Generally, monitoring of inorganic scale is most efficiently achieved using quartz crystal microbalance ("QCM") based technologies. Applicability of QCM-based instruments is determined, however, by sensor crystal stability under process conditions. Such instruments cannot be used under high temperature and/or high alkalinity conditions. This limitation makes the technology useless in digesters and evaporators. Besides a simple gravimetric technique and a non-quantitative characterization using Lasentec-FBRM, a technique based on deposit accumulation on the heated surface was proposed for liquors with solid content higher than 55% ("Method of monitoring and inhibiting scale deposition in pulp mill evaporators and concentrators," U.S. Pat. No. 8,303,768. However, this method is capable of detecting only sizable volumes of the deposit that makes it unusable in kraft mill digesters where calcium carbonate accumulation is too slow for the method of such a low sensitivity.

There thus exists an ongoing need to develop sensitive methods of monitoring deposits in the pulp and paper industry under the conditions of high temperature, alkalinity and pressure. Such monitoring is of particular importance in pulp mill digesters, evaporators and concentrators. The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 CFR §1.56(a) exists.

BRIEF SUMMARY OF THE INVENTION

To satisfy the long-felt but unsolved needs identified above, at least one embodiment of the invention is directed towards a method of monitoring the accumulation of scale on a surface in contact with a liquid medium. The method comprising the steps of: providing a refractometer having an photon emission source, a prism which emitted photons pass through, and an optical sensor constructed and arranged to detect photons that are refracted through the prism, the prism having at least one measuring surface; positioning the measuring surface relative to the medium such that emitted photons will be refracted as a result of the properties of the medium; determining a control critical angle of refraction for the medium for photons emitted by the emission source; emitting photons from the emission source; measuring the cell fouling factor of the measured critical angle of refraction relative to the control critical angle; and calculating the scale formation based on the measured cell fouling factor.

At least one embodiment of the invention is directed towards a method of measuring the effectiveness of a scale control agent. The method comprises the steps of: providing a refractometer having an photon emission source, a prism which emitted photons pass through, and an optical sensor constructed and arranged to detect photons that are refracted through the prism, the prism having at least one measuring surface; positioning the measuring surface relative to the medium such that emitted photons will be refracted as a result of the properties of the medium; determining a control critical angle of refraction for the medium for photons emitted by the emission source; adding a scale control reagent to the liquid medium; emitting photons from the emission source; measuring the cell fouling factor of the measured critical angle of refraction relative to the control critical angle, and calculating the effectiveness of the scale control reagent based on the measured cell fouling factor.

The invention encompasses the performance of its steps in any and all variations of order and sequence.

Additional features and advantages are described herein, and will be apparent from, the following Detailed Description.

BRIEF DESCRIPTION OF THE DRAWINGS

A detailed description of the invention is hereafter described with specific reference being made to the drawings in which.

For the purposes of this disclosure, like reference numerals in the figures shall refer to like features unless otherwise indicated. The drawings are only an exemplification of the principles of the invention and are not intended to limit the invention to the particular embodiments illustrated.

DETAILED DESCRIPTION OF THE INVENTION

Figure 1:
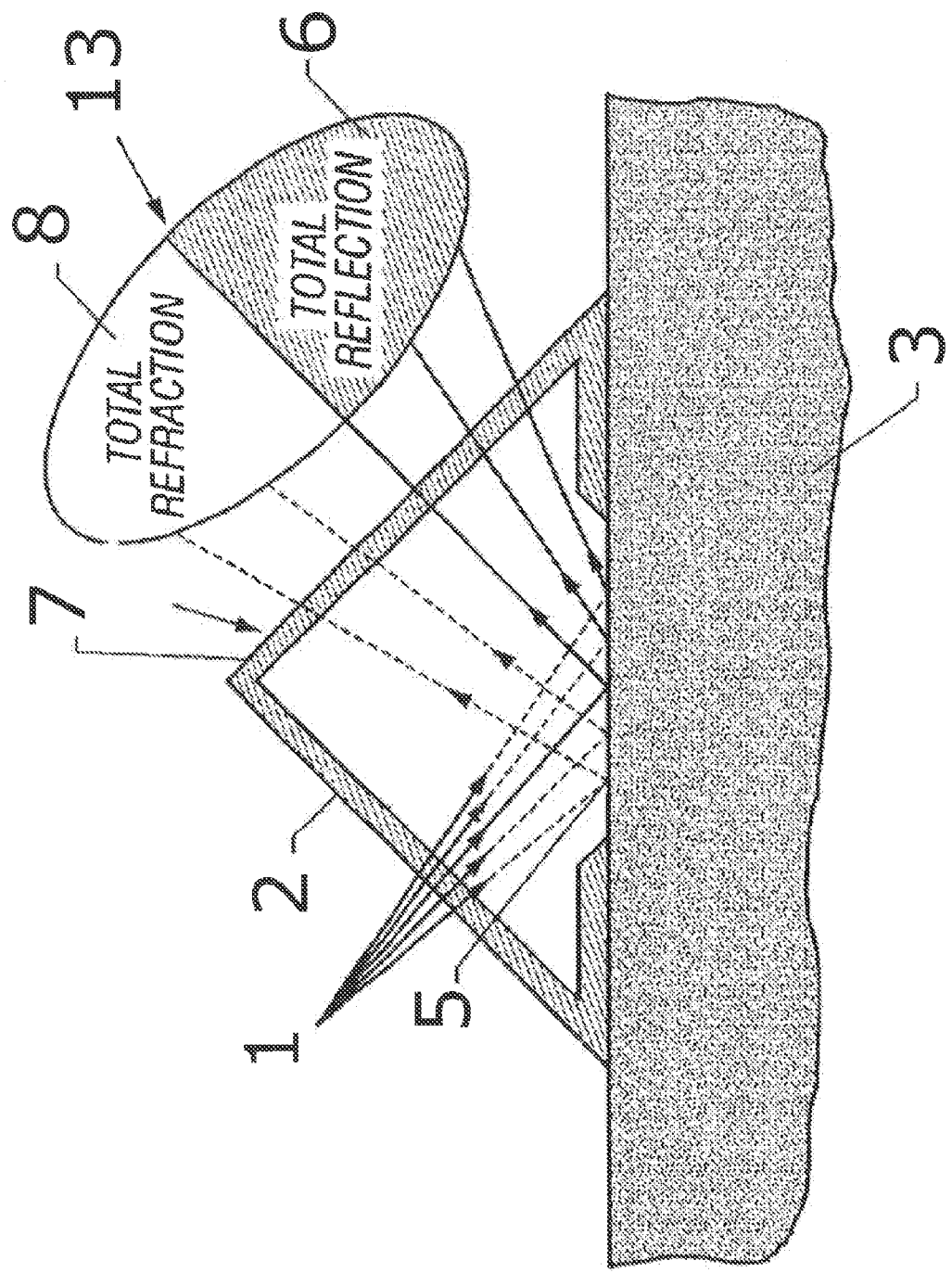
FIG. 1 is an illustration of using a refractometer to detect the critical angle of refraction used in the invention.

The following definitions are provided to determine how terms used in this application, and in particular how the claims, are to be construed. The organization of the definitions is for convenience only and is not intended to limit any of the definitions to any particular category.

"Consisting Essentially of" means that the methods and compositions may include additional steps, components, ingredients or the like, but only if the additional steps, components and/or ingredients do not materially alter the basic and novel characteristics of the claimed methods and compositions.

"Papermaking Process" means a method of making paper products from wood and wood products, it comprises one or more of: pulping wood, bleaching pulp, forming an aqueous cellulosic papermaking furnish from virgin or recycled wood pulp, draining the furnish to form a sheet, pressing the sheet to remove additional water, and drying the sheet. The steps of pulping wood, forming the papermaking furnish, draining, pressing, and drying may be carried out in any conventional manner generally known to those skilled in the art. The papermaking process also refers to pulp making.

"Surfactant" is a broad term which includes anionic, nonionic, cationic, and zwitterionic surfactants. Enabling descriptions of surfactants are stated in *Kirk-Othmer, Encyclopedia of Chemical Technology*, Third Edition, volume 8, pages 900-912, and in *MCutcheon's Emulsifiers and Detergents*, both of which are incorporated herein by reference.

"$\Phi$CRIT" means critical angle of refraction.

"Cell Fouling Factor" means the accuracy of a measurement taken according to a refractometry measurement where the accuracy may be decreased due to errors in the measurement caused at least in part by scale accumulation on the refractometer, cell fouling factor can be expressed in a number of ways including but not limited to percent deviations from the correct measurement value, it may be caused at least in part by such phenomenon as light scattering and light blocking by cell fouling of a transparent or light absorbing portion of a sensor.

"Cell Fouling" or "Scale" means the accumulation of at least partially solid matter on the surface of at least a portion of a piece of equipment within a process system, it includes but is not limited to inorganic deposits, organic deposits, microbiological deposits, and any combination thereof, its formation commonly occurs on surfaces in contact with process water or liquids, and vary based on process conditions such as variations and durations of temperature, chemical composition, exposure to sunlight or environmental factors, pH, and process media, it can be a problem in such industries including but not limited to pulp & paper, petroleum processing, mining, food processing, boilers, cooling water systems.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Darner Encyclopedia of Chemical Technology*, 5th Edition, (2005), (Published by Wiley, John & Sons, Inc.) this definition shall control how the term is to be defined in the claims.

At least one embodiment of the invention is directed towards the detection of scale in a process liquid system using changes in the cell fouling factor of the critical angle of refraction of the liquid ($\Phi_{CRIT}$). As described for example in U.S. Pat. Nos. 6,387,705, 4,776,697, 4,571,075, 5,815,264, 5,859,705, 6,819,419, and 7,094,562 refractometry can be used to determine properties of a liquid.

As illustrated in FIG. 1, in an ideal refractometry arrangement an emission source (1) discharges photons through a prism (2) and at a liquid medium (3). Some of the discharged photons are absorbed by the medium (3) and some are refracted back through the prism towards an emission sensor (4). The difference in the nature of refraction between a control liquid, and a measured liquid can be used to determine various properties of the liquid such as the type and amount of particles present in the liquid.

Refractometry measurements rely on the calculation of a critical angle of refraction or $\Phi_{CRIT}$. For any given prism there is a lowest possible angle of refraction relative to the measuring surface of that prism (5). This is because at angles lower than this angle, the alteration of the direction of a photon is such that it does not remain within the prism but passes into the liquid medium. The $\Phi_{CRIT}$ is the lowest measured angle of reflected photons that pass through the prism's exiting surface (7) for a given sample, $\Phi_{CRIT}$ varies depending on the properties of the prism and the liquid medium.

Figure 2:
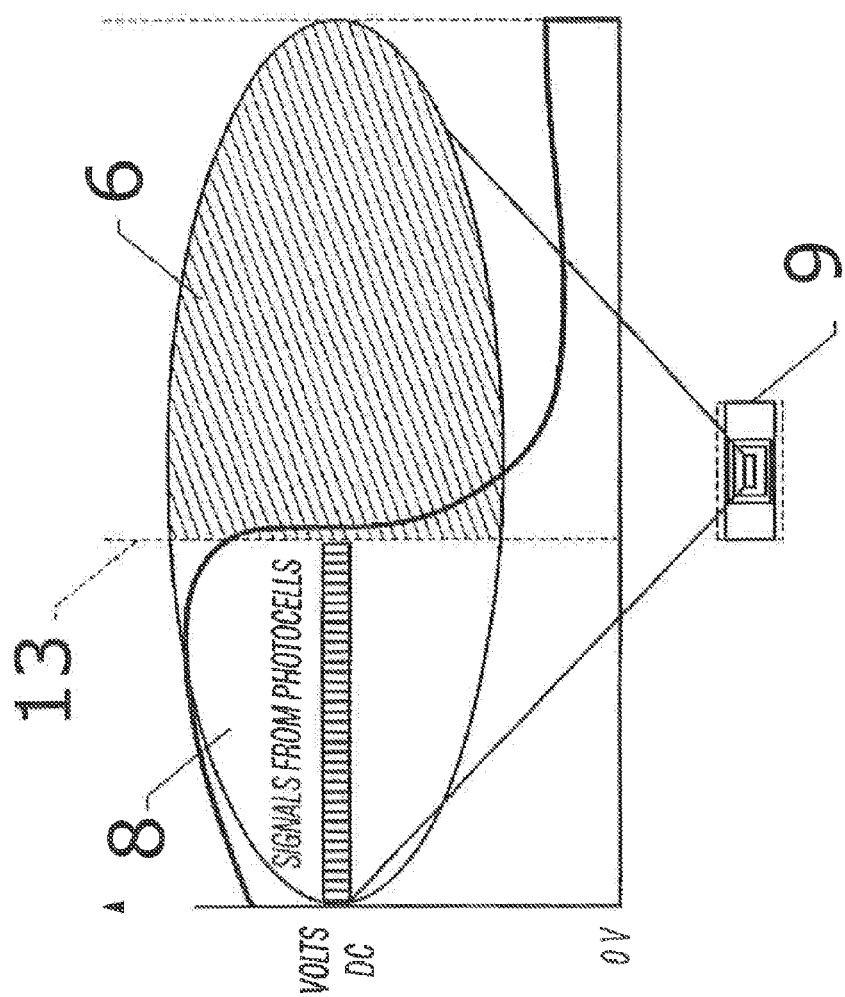
FIG. 2 is an illustration of using a refractometer to measure the transition point used in the invention.

Referring now to FIG. 2 there is shown a manner in which $\Phi_{CRIT}$ can be represented graphically. As described in more detail in U.S. Pat. No. 6,387,705, portions of the light rays that are at angles larger than $\Phi_{CRIT}$ are reflected by the measuring surface (5) of the prism towards an image detector (not shown in this figure). Rays incident on measuring surface (5) at angles smaller that the $\Phi_{CRIT}$ refract in the process medium (3) in contact with measuring surface (5) and are not reflected. Basically, this narrow bandwidth beam is emitted by emission source (1) and is directed onto measuring surface (5) where some of the beam that is larger than $\Phi_{CRIT}$ will be reflected back by the surface (5) and to total reflection area (6). Rays that arrive at an angle to measuring surface (5) that are smaller than the minimum angle will be refracted out the prism (2) via exit surface (7) to total refraction area (8). The beams reflected back to the base by measuring surface (5) can be detected by detector (9) and the critical angle determined by the amount of light detected by detector (9).

The $\Phi_{CRIT}$ will be dependent on the refractive index of the prism (2) and on the refractive index of material in contact with measuring surface (3). Therefore, the refractive index of a liquid in contact with measuring surface (3) can be determined from the photons measured by detector (9) by finding the critical area of the transition point (10). Due to the small change in refractive index of various solutions introduced during operation of the present invention, the change in position of the boundary between refracted (12) and reflected rays (11) is also very small.

As illustrated in FIG. 2, in the optical detector, the use of image detector (9) and image digitizer will find the bright-dark boundary that is the transition point (10) using a fitting method. In at least one embodiment the fitting method includes but is not limited to linear interpolation, polynomial-curve interpolation, or any combination thereof. The term "bright-dark boundary" or transition point (10) as used herein means the boundary between a region of total photon reflection (6) and a region of total refraction (8). Along the bright-dark boundary or transition point (10), a Fresnel diffraction phenomenon may occur, in at least one embodiment in determining the bright-dark boundary, it is convenient to exploit the Fresnel diffraction phenomenon in which the quantity of photons in the measured waveform is always increased beyond that of the reference emission. The point of intersection closest to the portion where the photon quantity has increased between the reference waveform and the measured waveform is read out as the bright-dark boundary or transition point (10).

In at least one embodiment the image detector (9) captures the photons that are in turn processed by image digitizer to form voltage signals from the photocells can be divided into the three regions. These regions relate to the total refraction region (8), the total reflection region (6) and the transition point or bright-dark boundary (13). In at least one embodiment the image digitizer locates the region (13) by noting the voltage shift from nearly about one-volt in the preferred embodiment to significantly less as shown herein.

Refrectometry measurements can be made imprecise by the presence of scale on the refractometer. For example in a measurement of a given sample in which the particle composition of the liquid does not change but the temperature of the liquid changes, the measured $\Phi_{CRIT}$ changes drastically. Once however the refractometer was washed with acid, even at the high temperature the measured $\Phi_{CRIT}$ returns to the correct value. The accuracy of the measured $\Phi_{CRIT}$ relative to the actual $\Phi_{CRIT}$ is the cell fouling factor.

Without being limited by a particular theory or design of the invention or of the scope afforded in construing the claims, it is believed that because scale is often inversely soluble relative to temperature, the cell fouling factor of the refractometer decreases due to the accumulation of scale on the measuring surface which altered the refractive properties of the prism.

In at least one embodiment the change in the cell fouling factor can be used to detect and measure the accumulation of scale in a system. In at least one embodiment the refractometer can be positioned anywhere in a process system.

The detection of scale by a refractometer can be complicated by properties innate to scale formation. For example, often scale most readily accumulates in extremely harsh environments where a detector cannot easily be positioned or read or were the refractometer itself would not long survive such as for example in a high temperature reactor or in a pulp digester. As a result, in at least one embodiment a refractometer is positioned in contact with a sample that is compositionally identical to one elsewhere and which can be used to predict the presence of scale in that other location.

For example, in at least one embodiment at least a portion of a refractometer (such as but not limited to the measuring surface) is heated and a change in cell fouling factor is looked for. A change in cell fouling factor would indicate that this same sample when exposed to that temperature would undergo scale formation. In at least one embodiment the relative differences between the propensity for scale formation of the material the process fluid is within and the propensity for scale formation of the portion of the refractometer need to be taken into account. As a result, the likelihood of a sample to form scale when it passes onto a different point in an industrial process with a different temperature can be predicted by applying a representative temperature change to the refractometer.

In at least one embodiment the method is used to predict the presence of scale in such processes as papermaking, pulping including kraft pulping, bleaching, pulp mill recovery process, and also, beyond pulp and paper application area, encompass more applications where scale/deposit monitoring is critical, e.g., boilers, cooling towers, mining (Bayer processing of alumina), oil industry, etc. The liquid medium may be such items as black liquor in pulping and Bayer liquor in aluminum manufacturing.

In at least one embodiment the refractometer is positioned upstream or downstream from a process stage that is susceptible to scale formation.

In at least one embodiment the refractometer is not cleaned from scale so as to allow for accurate calculations of scale.

This invention makes use of a novel and unexplained phenomenon which is taught away by the prior art. Standard refractometry techniques take for granted that the measuring surface must be kept clean so they effectively teach away looking to what in effect are errors to predict scale formation. The prior art has mentioned a correlation between scale formation and optical properties, for example, in the scientific paper *Assessment of an Intrinsic Optical Fiber Sensor for in Situ Monitoring of Scale-Forming Salts*, by Wallace, Andrew D., Boerkamp, Martijn, Lye, Peter G., Lamb, David W., Doherty., William O. S., Fellows, Christopher M., Industrial & Engineering Chemistry Research, Vol. 47 Issue 4, pp. 1066-1070 (2008) (hereinafter "Wallace"). Wallace, however, makes no mention of using refractometry to simulate scale formation in other locations of a process system, makes no mention of heating the refractometric sensor, makes no mention of using the refractometer to detect scale which is inversely soluble to temperature (it measure scale proportional to temperature) and most of all teaches away using the refractometer in harsh conditions because such conditions "irreversibly damage" and "exceed the glass transition temperature" of its optical sensors. Id, at 1069.

In at least one embodiment in response to the measured or predicted scale a scale remediation program is activated or enhanced. Such remediation includes the addition of scale inhibiting or removing materials. The scale inhibiting or removing materials can be introduced or the dosages changed as a preemptive, or responsive reaction to the measurement or prediction of scale.

In at least one embodiment the scale is at least in part: caused by and/or causes the consequences and/or is remediated by at least one of those items described in one or more of: *Low-cost evaporator upgrades boost performance, reduce scaling*, by Adams, R. W., Pulp Paper, Volume 73 issue 2, pp. 83-89 (1999), *Scale deposit problems in pulp and paper mills*, by Sitholé, B, Proc. African Pulp and Paper Week, Durban, S A (2002). *The effects of wood extractives on system closure*, by Sithole, B. B., Allen, L, TAPPSA Journal. Volume 9, (2002), *Water-Formed Scale Deposits*, by Cowan, J. C., Weintritt, D. J, Gulf Publ. Co., Houston, Tex. (1976), *Mechanism and chemical control of $CaCO_3$ scaling in the kraft precess,* by Severtson, S. J., Duggirala, P. Y., Carter, P. W., Reed, P. E., TAPPI J., Volume 82 Issue 6, pp. 167-174 (1999), *Measuring the response of pitch control strategies*, by Garver, T. M., Yuan, H, Pulp Paper Canada, Volume 103 Issue 9, pp. 24-28 (2002). *The distribution of calcium in kraft mill brownstock systems*, by Douek, M.; Allen, L. H., Sven, Papperstidn Volume 83 Issue 15, pp. 425-429 (1980), and U.S. Pat. Nos. 3,433,603 and 5,254,286. In at least one embodiment the use of the invention predicts, detects, measures, reduces and/or eliminates one or more of such problems.

Scale formation on wood processing equipment often brings inefficiencies to the pulping process because of downtime losses, higher utility costs, and corrosion. In at least one embodiment the use of the invention predicts, detects, measures, reduces and/or eliminates one or more of such problems.

In the context of papermaking, scale formation from mill waters on equipment complicates plant operations. First, it affects operational efficiency reducing heat transfer obstructing washer wires, blinding of screens, constricting stock and liquor flows, and eventually resulting in a significant equipment downtime for scale removal. Second, it affects pulp quality producing an off-spec product due to sheet defects and high dirt count, and also increases levels of anionic trash and colloidal contaminants. Eventually, it negatively affects pulping and bleaching cost due to high energy costs, lost production and reduced production rates, and downtime for scale removal. In at least one embodiment the use of the invention predicts, detects, measures, reduces and/or eliminates one or more of such problems.

The mechanisms of scale formation and approaches to control different kinds of scale are different. As a result in at least one embodiment a multicomponent scale control program is used. A particularly troublesome form of scale formation is at the digester and bleach plant of a papermaking plant. Such scale can be inorganic, though organic scale originating from wood pitch and from process chemicals may compound the problem and occasionally become a separate issue (e.g., in brownstock washers); in recycle plants the most important scales are organic. The most common inorganic scales at bleach plants are calcium carbonate, calcium oxalate and barium sulfate, in a digester it is calcium carbonate. Often scales are of mixed nature because scale that has accumulated from one type of component can form an excellent base for other scales to grow on. Organic admixtures in an inorganic scale are a common phenomenon. Fiber can be easily trapped by growing crystals and then form a base for new crystals to grow. In at least one embodiment the use of the invention predicts, detects, measures, reduces and/or eliminates one or more of such problems.

The driving force for scale formation is exceeding solubility limits of the scale components. The initial steps of ion pairing and nucleation, involve adsorption of the scale components onto a surface. The adsorption process continues yielding ion clusters on the surface. The same process takes place in the bulk solution yielding dispersed clusters and microcrystals that may either stay in the solution causing no harm or attach to crystallization centers on the surface increasing the volume of scale. The ion clusters grow into microcrystals on the surface, usually at surface imperfections. They become crystallization centers for further, accelerated scale growth. Scale growth continues via ion pairing or nucleation. Ion by ion growth occurs as ion clusters continue to be adsorbed by the existing nuclei on the surface. In nucleus-to-nucleus growth, nuclei are formed in the bulk phase of the solution prior to their attachment to the surface nuclei. These nuclei are larger in size than ion cluster and consequently build-up a rougher, imperfect scale on the surface. In addition, any crystals that are formed in solution may also become entrapped within the rapidly growing scale matrix resulting in a mixed scale. In at least one embodiment the use of the invention predicts, detects, measures, reduces and/or eliminates one or more of such problems.

Organic deposit scale in the papermaking process may originate either from wood (wood pitch) or from paper additives that are released during recycling (white pitch, stickies). Wood pitch primarily consists of fatty acids and their salts, waxes, and other hydrophobic organic materials. It forms microscopic particles that easily agglomerate. The saponifiable portion of pitch is sensitive to the conditions, and tends to deposit at lower pH and in the presence of divalent metal cations. Unsaponifiable neutral organics are, generally, insoluble and present in an unstable, colloidal state that can readily form deposits. Deposition starts when large agglomerates form from small colloidal particles. Significant amounts of calcium were found in pitch deposits from the brownstock systems of kraft mills. As a composition example, the deposit characterized in that paper was 1.6% wood resin, 30% metal soaps (mostly calcium soaps), 38% calcium carbonate, and 16% silica and fibers. Typically, the deposits are of mixed nature. Pitch control chemicals affect both colloidal stability and concentration of pitch, in at least one embodiment the use of the invention reduces or eliminates such problems. In at least one embodiment the use of the invention predicts, detects, measures, reduces and/or eliminates one or more of such problems.

EXAMPLES

The foregoing may be better understood by reference to the following examples, which are presented for purposes of illustration and are not intended to limit the scope of the invention.

An experimental setup was built as an example of the embodiment that combined a circulation system and heated refractometric sensor built of material that can sustain conditions of high alkalinity. The setup was expected to be representative of an industrial environment where high temperatures, pressures, and alkalinities are present. This setup indeed produced temperature-induced calcium carbonate deposition on the heated sensor when concentrations of calcium and carbonate ions allowed. This was borne out by references to FIG. 3-7 which show that as temperature goes up, scale goes up and the cell fouling factor increases and needs to be corrected for.

A number of samples were measured using an on-line refractometric sensor providing continuous stream of data, which was used to determine the cell fouling factor and refraction index. In a first test the sensor was immersed in a supersaturated solution of calcium bicarbonate (16 mM based on calcium chloride and sodium bicarbonate) at the top of the SRM-3 instrument (Nalco-Ecolab Company) cell. Scale was induced by supersaturation all over the cell including the refractometric and QCM sensors. Both sensors demonstrated similar trends in scale formation. The accumulated scale resulted in drastic changes in the cell fouling factor which were proportionally related to the scale formation as independently measured by the SRM-3 instrument based on a microbalance technology.

Figure 6:
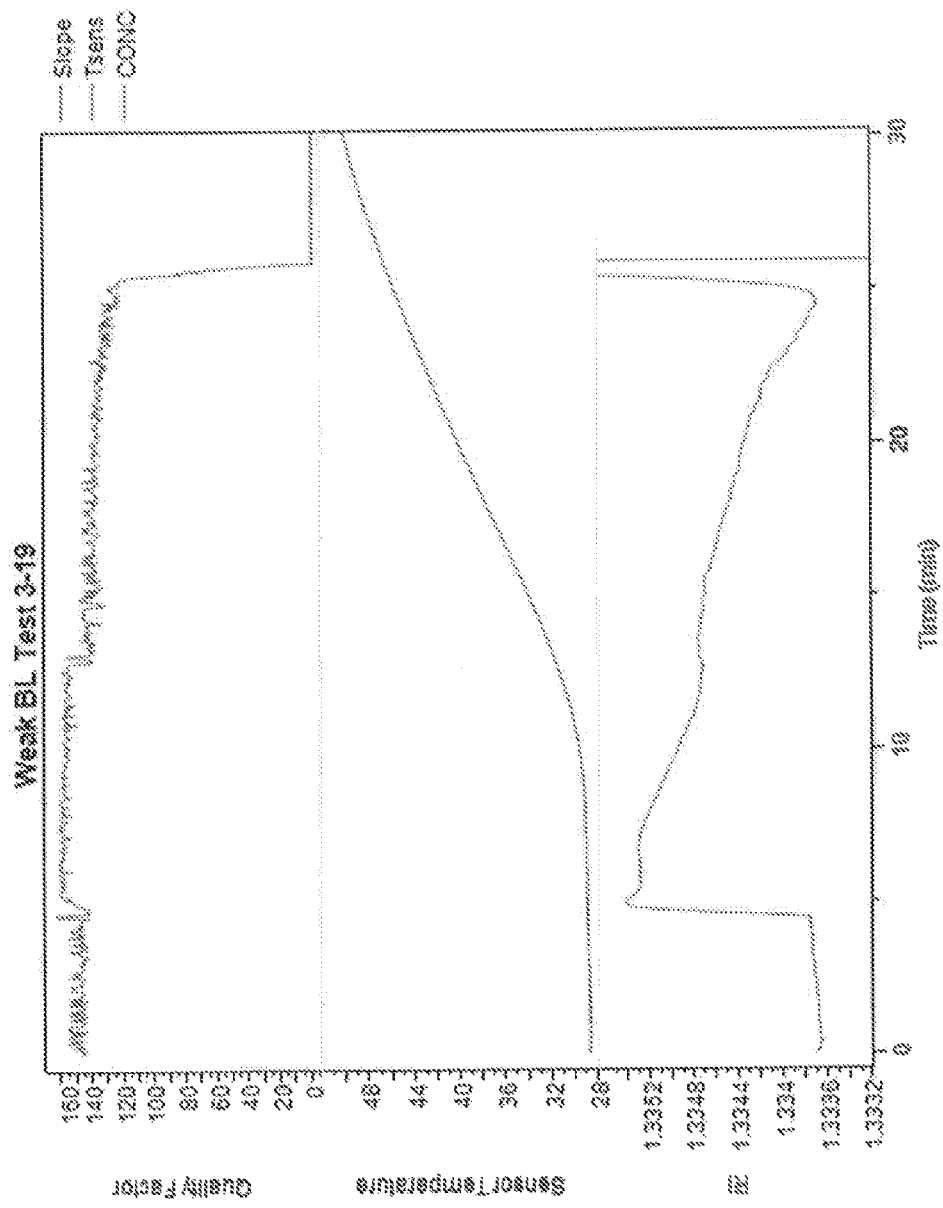
FIG. 6 is a graph showing scale accumulation from dilute black liquor as measured by the scale index (reverse cell fouling reading).
Figure 7:
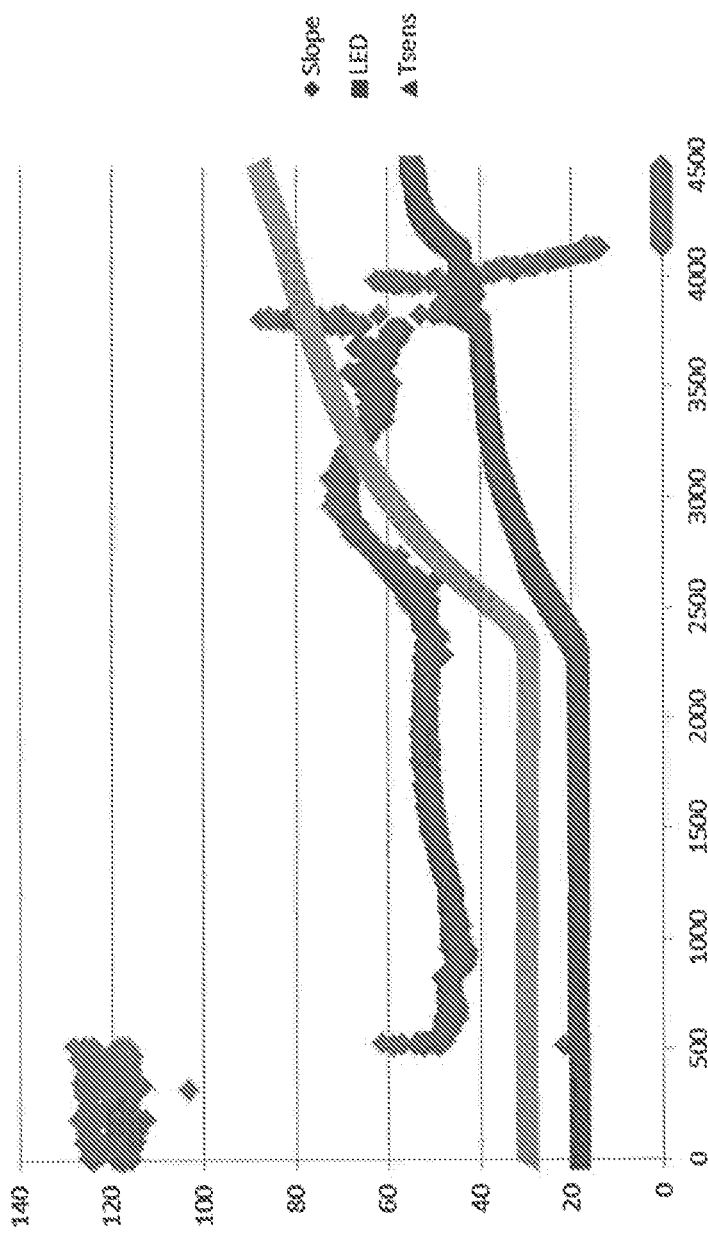
FIG. 7 is a graph showing scale accumulation from standard black liquor supersaturated with sodium carbonate and calcium chloride, as measured by the scale index (reverse cell fouling reading).

In a second example, the sensor was continuously heated under control in a low-through arrangement, while the temperature of the solution was maintained at a room temperature level by an improvised thermostat so that the temperature gradient would be maintained at 60 C. In this case, lesser concentration of calcium bicarbonate (4 mM based on calcium chloride and sodium bicarbonate) was applied. The temperature-induced deposition was recorded (FIGS. 4-5); application of an excess of hydrochloric acid after the test completely removed the deposit that was reflected in the instrument readings. The same experiment was repeated in presence of 20 and 5 ppm of ScaleGuard60116. which effect is clearly demonstrated (same figures). Scale formation was also detected in a dilute black liquor (1.0% in water) under the same conditions (FIG. 6). Notice though that in that case the pattern of changes in the cell fouling is different. The plot shows the rapid drop of the cell fouling when the scale forms in a quantity sufficient to block the sensor window. The initial increase in refractive index is due to the addition of carbonate to the weak BL solution. The sharp drop in cell fouling factor is due to the addition of calcium.

Figure 3:
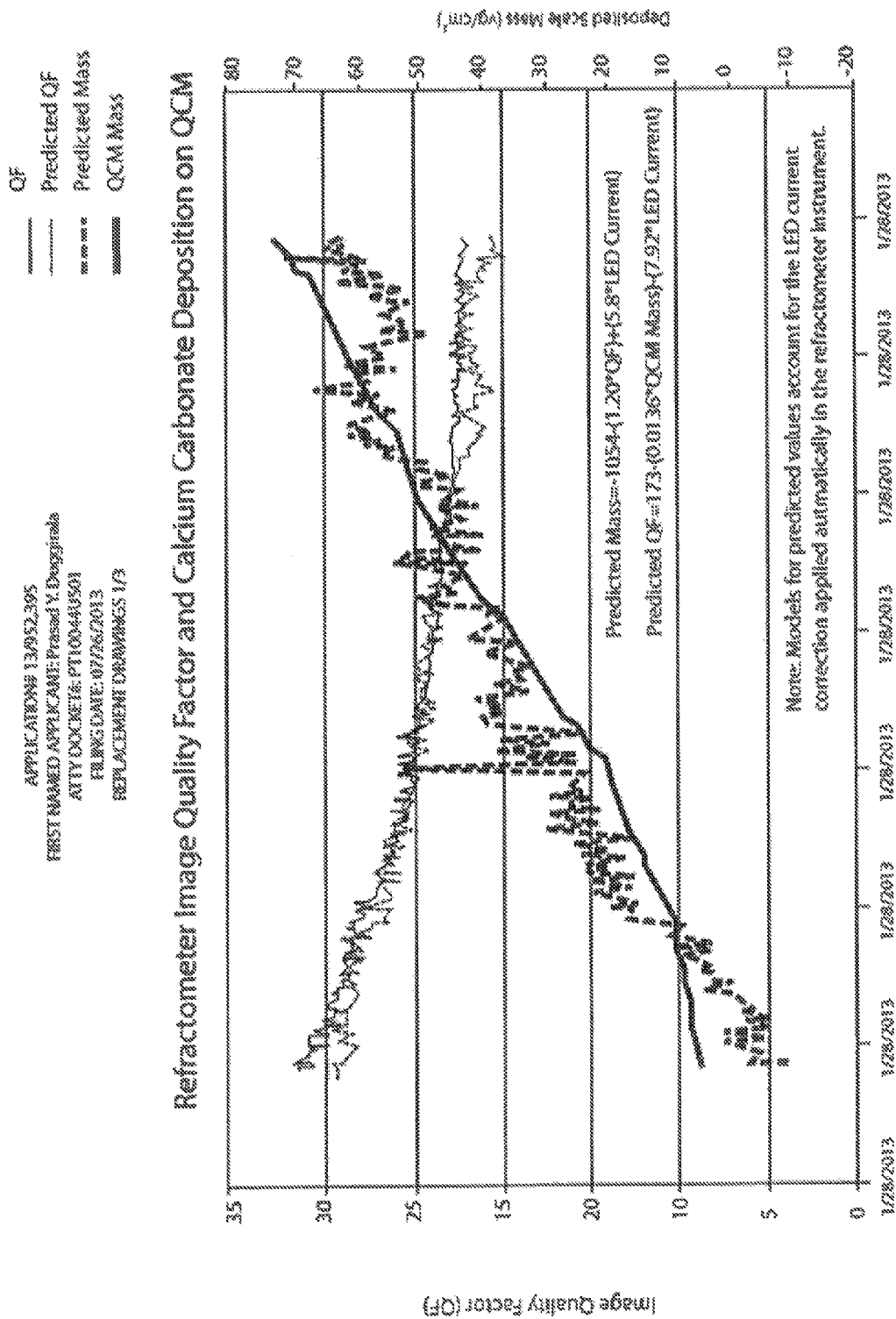
FIG. 3 is a graph showing a correlation between the cell fouling ("cell fouling factor") and scale accumulation measured independently using an SRM-3 instrument.
Figure 4:
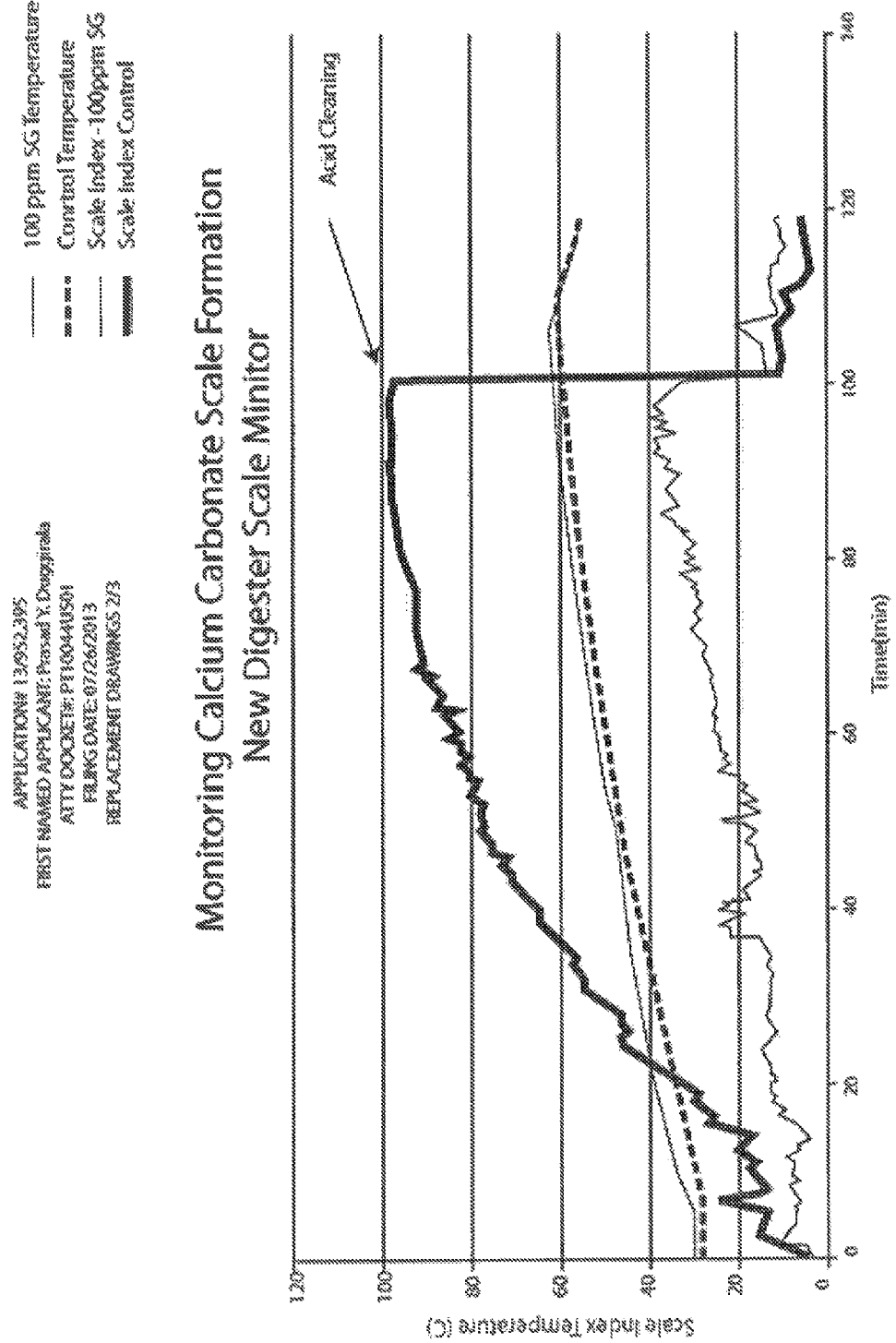
FIG. 4 is a graph showing scale accumulation from a model calcium bicarbonate solution as measured by the scale index (reverse cell fouling reading) and the effect of a scale inhibitor on scale accumulation as measured by the same parameter.
Figure 5:
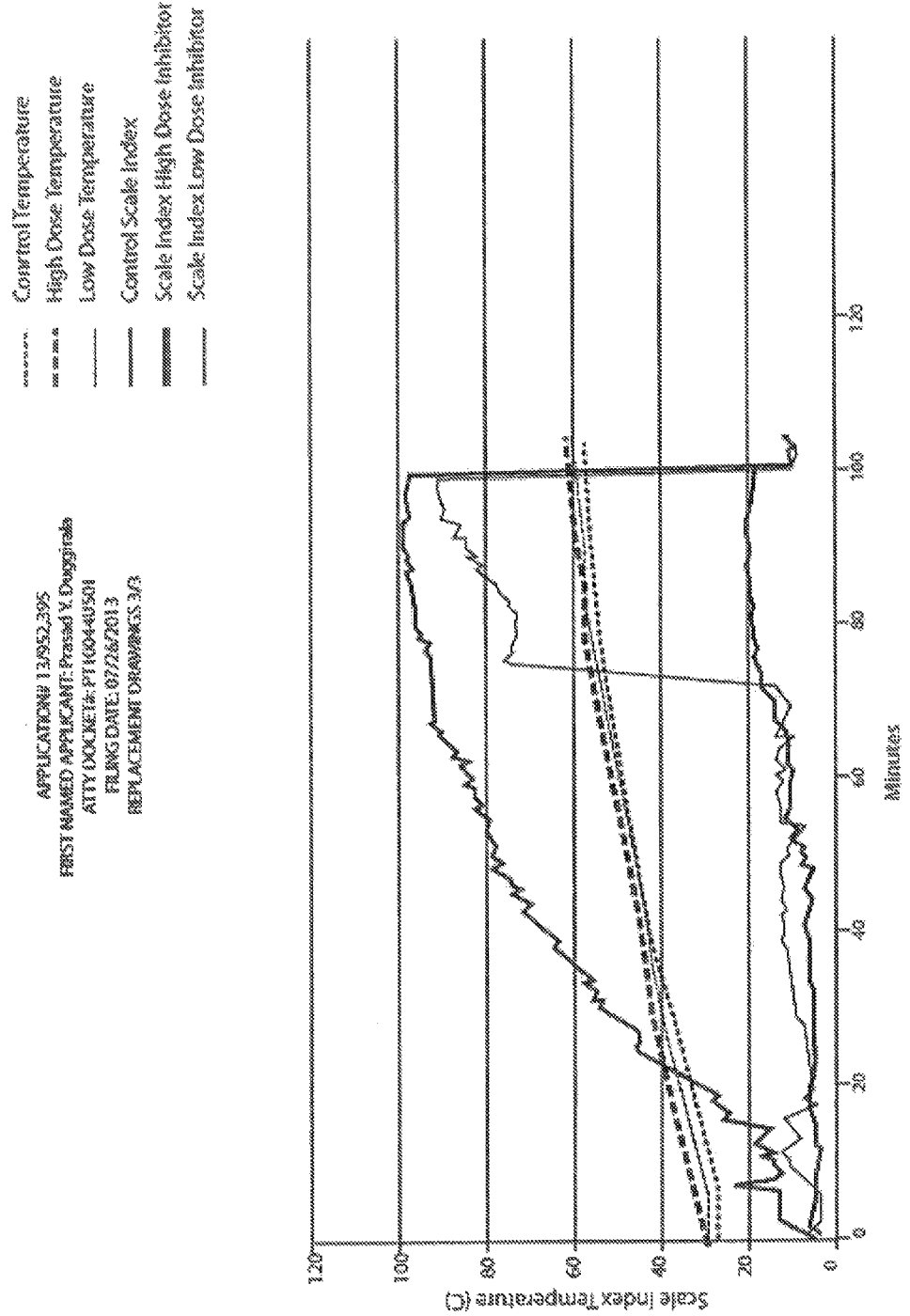
FIG. 5 is a graph showing the effect of a scale inhibitor at different doses on scale accumulation from a model calcium bicarbonate solution as measured by the scale index (reverse cell fouling reading); acid cleaning of the sensor occurs in the end.

In a third example, the sensor was continuously heated under control in a flow-through arrangement with real kraft pulping black liquor (15% solids) saturated with sodium carbonate, with continuous dropwise addition of 10% solution of calcium chloride. The temperature of the solution was maintained at approximately 40 C level by an improvised thermostat so that the temperature gradient would be maintained at 40-60 C (FIG. 3,4). The temperature-induced deposition was recorded (FIG. 7); application of an excess of hydrochloric acid after the test completely removed the deposit that was reflected in the instrument readings.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments mentioned herein, described herein and/or incorporated herein. In addition the invention encompasses any possible combination that also specifically excludes any one or some of the various embodiments mentioned herein, described herein and/or incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range. All percentages, ratios and proportions herein are by weight unless otherwise specified.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A method of monitoring the accumulation of scale on a surface in contact with a liquid medium, the method comprising the steps of:
   positioning a refractometer adjacent to the liquid medium;
   emitting photons into the refractometer;
   calculating a cell fouling factor; and
   calculating the area of scale formation based on the calculated cell fouling factor;
   wherein:
      the refractometer has a photon emission source, a prism which the emitted photons pass through, and an optical sensor constructed and arranged to detect photons that are refracted through the prism, the prism having at least one measuring surface:
      the emitted photons are emitted by the emission source, the measuring surface is positioned relative to the liquid medium such that angles of refraction of the emitted photons will depend on the properties of the medium, the angles of refraction of the photons determining what is detected by the optical sensors;
      the cell fouling factor is the percent deviation between what is detected by the optical sensor in a given measurement and a control value; and
      the control value is the measurement of what would be detected by the optical sensor for the same medium when there is a known amount of scale on the measuring surface.

2. The method of claim 1 in which the control value and the given measurement are measured by determining a bright-dark boundary between reflected and refracted photons from a measuring surface of the prism and correlating the bright-dark boundary to the concentration of particular particles in the liquid medium.

3. The method of claim 1 in which the refractometer is used to measure the accumulation of temperature dependent scale formation wherein the refractometer is positioned at a location where the medium is not at a sufficient temperature to form scale and the refractometric sensor is heated.

4. The method of claim 3 in which the refractometer sensor is heated to correspond to the temperature present at another location within the process system.

5. The method of claim 3 in which the refractometer comprises a heat conducting metal body with a small window made of an alkali-resistant material and heat is applied to the body.

6. The method of claim 3 in which the measuring surface is heated.

7. The method of claim 3 in which the refractometric sensor is made of materials that withstand harsh conditions of kraft pulping, evaporators in pulp and paper and sugar processing industries or a Bayer process in mining.

8. The method of claim 3 in which the calculation is corrected for differences in the propensity of the measuring surface to accumulate scale and the propensity for scale to form on at least one other material which a surface of a piece of equipment in the process system is constructed out of.

9. The method of claim 1 in which the measuring surface is heated where scale formation is monitored continuously, with express cleaning of the refractometer through physical (e.g., ultrasound) or chemical (acid or/and chelant injection) through regular intervals.

10. The method of claim 1 in wherein the scale is one selected from calcium carbonate, calcium oxalate, calcium sulfate, calcium sulfite, barium sulfate, magnesium silicate, sodium carbonate/sodium, burkeite, and any combination thereof.

11. The method of claim 1 wherein the liquid medium is one item selected form the list consisting of: black liquor, pulping liquor, digester liquid, evaporator liquid, bleaching liquor, recovery water, papermaking water, liquid from waste treatment stages of the pulp and paper making processes, industrial process liquid, ore processing liquid, oil refining process liquid, oil extraction process liquid, oil transporting process liquid, cooling tower water, boiler water, food sanitizing liquid, ore slurry, and any combination thereof.

12. The method of claim 1 wherein the refractometer is positioned at a sidestream diverted out of the process system.

13. The method of claim 1 in which the optical sensors detect photons that are refracted by the liquid medium but not photons that are reflected by the liquid medium.

14. The method of claim 1 in which the control value is the measurement of what would be detected by the optical sensor when there is substantially no scale on the measuring surface.

15. The method of claim 1 in which the control value is the measurement of what would be detected by the optical sensor when there is some scale on the measuring surface.

16. The method of claim 1 in which the optical properties of the control value and the given measurement is the lowest measured angle of refracted photons detected by the optical sensors.

17. The method of claim 1 in which the optical properties of the control value and the given measurement measured by the optical sensor is the lowest measured angle of refraction of the emitted photons.

18. The method of claim 1 further comprising the step of adding a scale control agent to the medium in response to the cell fouling factor exceeding a first pre-determined value.

19. The method of claim 18 further comprising the step of halting the addition of scale control agent to the medium in response to the cell fouling factor lowering to a second pre-determined value.

* * * * *